United States Patent [19]

Tamaoki

[11] Patent Number: 4,709,014

[45] Date of Patent: Nov. 24, 1987

[54] PREPARATION OF PEPTIDES WITH C-TERMINAL PROLINE AMIDE

[75] Inventor: Hidetsune Tamaoki, Hiromachi, Japan

[73] Assignee: Sankyo Company Limited, Tokyo, Japan

[21] Appl. No.: 846,877

[22] Filed: Apr. 1, 1986

[30] Foreign Application Priority Data

Apr. 8, 1985 [JP] Japan .................................. 60-72705

[51] Int. Cl.$^4$ .......................... C07K 1/02; C07K 5/08; C07K 5/10; C07K 7/08; C07K 7/06; C07K 7/38; C07K 7/16; C07K 7/20

[52] U.S. Cl. .................................... 530/333; 530/307; 530/313; 530/315; 530/324; 530/325; 530/326; 530/327; 530/328; 530/329; 530/330; 530/331

[58] Field of Search ............... 530/333, 315, 313, 307, 530/324, 325, 326, 327, 328, 329, 330, 331

[56] References Cited

U.S. PATENT DOCUMENTS 4,654,302  3/1987  Fritz et al. ........................... 530/324

Primary Examiner—Delbert R. Phillips
Attorney, Agent, or Firm—Frishauf, Holtz, Goodman & Woodward

[57] ABSTRACT

A peptide with C-terminal proline amide is produced by reacting in aqueous solution a protein substrate having C-terminal prolyl-leucine, prolyl-isoleucine, prolyl-valine, or prolyl-phenylalanine with carboxypeptidase Y in the presence of ammonia. The ammonia is preferably generated by the aqueous reaction of an ammonium salt and an alkali. An example of the peptide product is human calcitonin.

6 Claims, No Drawings

PREPARATION OF PEPTIDES WITH C-TERMINAL PROLINE AMIDE

BACKGROUND OF THE INVENTION

This invention relates to the preparation of peptides with C-terminal proline amide.

Many peptide hormones of relatively small molecular size carry an α-amide substituent at the C-terminus of the peptide chain, and this amide group is believed generally to play an important role in their biological activity. It is thought that these C-terminal amide groups are formed enzymatically after biosynthesis of the peptide chain — A. F. Bradbury et al, Nature, 298, 686 (1982). Although some proteins and peptides can now be produced by genetic engineering techniques, amidation of the C-terminal amino acid similarly has to be performed as a separate step after the synthesis of the peptide chain. There is, accordingly, a need for effective amidation techniques which can be used to produce such peptides with an amide group at the C-terminus.

Synthetic chemical means of amidation tend to be unsatisfactory for this purpose because they are generally insufficiently selective, giving rise to unwanted side reactions. There may also be a loss in the physiological activity of the peptide under such reaction conditions. Enzymatic techniques for the amidation are therefore to be preferred.

One such enzymatic technique uses porcine pituitary to convert peptides which terminate in glycine to the corresponding des-glycine peptide amides — A. F. Bradbury et al, Nature, 298, 686 (1982). Unlike the chemical amidation techniques, this enzymatic process is apparently selective and not accompanied by side reactions. On the other hand, the use of porcine pituitary does present several disadvantages, because the enzyme source is not readily available in commercial quantities, because it is difficult to obtain the enzyme in a sufficiently pure form, and because the enzyme is somewhat unstable. It should also be noted that this enzyme apparently has a requirement for C-terminal glycine in the substrate peptide.

Another enzyme which has been investigated for C-terminal amide formation in peptides is carboxypeptidase Y. This enzyme, which can be obtained from baker's yeast, is an exopeptidase and cleaves the C-terminal peptide bond to release successive amino acids from the C-terminus of the peptide chain. However, in common with other peptidases, this enzyme can also be used to catalyse the formation of peptide bonds — Kazuyuki Morihara, Protein-Nucleic Acid-Enzyme, 26, 1979 (1981). K. Breddam et al in Carlsberg Res. Commun. 46, 121 (1981) describe the use of carboxypeptidase Y to catalyse the exchange of C-terminal amino acid residues in peptides for various other groups, including the conversion of peptides to peptide amides. This reference states that the yield of the reaction is strongly dependent on the nature of the C-terminal amino acid residue.

The best yields are obtained with peptide substrates in which a hydrophilic amino acid (e.g. glycine) serves as the leaving group, and the lowest yields are obtained with substrates in which a hydrophobic amino acid (e.g. valine or phenylalanine) serves as the leaving group. It also states that the penultimate amino acid residue of the substrate exerts a pronounced influence on the yield; and there is no disclosure of any reaction using a substrate in which the penultimate amino acid is proline. This follows a general belief in the art that peptides having proline as the penultimate C-terminal amino acid residue are resistant to such reactions.

BRIEF DESCRIPTION OF THE INVENTION

In contrast to the method of Breddam et al, the present invention provides an amidation method catalysed by carboxypeptidase Y in which the penultimate amino acid residue at the C-terminus of the substrate is proline, and in which amidation takes place when the C-terminal leaving group attached to the proline residue is a specific hydrophobic amino acid but not when it is a hydrophilic amino acid such as glycine.

Accordingly, it is an object of the present invention to provide a specific enzymatic route for the preparatin of peptides with proline amide at their C-terminus. It is a further object of the invention to provide such a method which avoids the disadvantages of the previously known chemical and enzymatic amidation techniques.

In the process of the invention, the substrate used is a peptide having at its C-terminus prolyl-leucine, prolyl-isoleucine, prolyl-valine, or prolyl-phenylalanine. The reaction is performed by treating this peptide substrate with carboxypeptidase Y in the presence of ammonia, to give the corresponding peptide with C-terminal proline amide.

DETAILED DESCRIPTION OF THE INVENTION

The process of the invention can be summarised by the following reaction scheme:

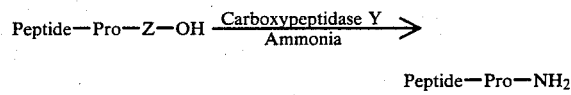

Peptide—Pro—NH₂ wherein "Pro" represents a proline residue and "Z" represents a residue of leucine, isoleucine, valine, or phenylalanine.

The peptide substrate may be subjected to the amidation reaction of the invention without any protection at its N-terminus. However, this terminus will often have been protected at an earlier stage in the synthesis of the peptide and may have on it a conventional protecting group, such as carbobenzoxy (i.e. benzyloxycarbonyl), acetyl, benzoyl or t-butoxycarbonyl. In such a case, it is not necessary to remove the N-terminal protecting group before subjecting the substrate to the amidation, since it does not interfere with the reaction.

Human calcitonin is a specific example of a peptide hormone which can be prepared by the process of the invention. This has a peptide chain of 32 amino acid residues, with Pro-NH₂ at its C-terminus. The peptide chain, with an additional C-terminal amino acid residue falling within the above definition of "Z", can be produced by genetic engineering techniques and then subjected to the amidation reaction.

The amidation reaction is performed in aqueous solution and can be effected by mixing previously prepared solutions of the peptide substrate, the carboxypeptidase Y and ammonia. A compound or compounds which will generate ammonia in situ may be used instead of ammonia itself. A temperature in the range of 25°–40° C. is suitable for the reaction and the optimum temperature is 37° C.

Since the peptide substrate is only sparingly soluble in water, it may be more readily dissolved by using an aqueous organic solvent, such as 40% aqueous dioxane or 40% aqueous dimethylsulfoxide, or by solubilising it in water with a suitable surfactant, such as sodium dodecylsulfate or octoxynol. The choice and concentration of organic solvent or surfactant should, of course, be such that it does not adversely influence the amidation reaction.

The molar ratio of carboxypeptidase Y to peptide substrate in the reaction solution is preferably within the range of 5-50:1000. If a higher concentration of enzyme is used, the yield of amidation product increases but there is also a marked increase in side reactions. On the other hand, increasing the relative amount of substrate also increases the amount of amidation product, but not in proportion with the increase in amount of substrate, so that the yield of amidation product relative to the substrate decreases.

The amidation reaction should be performed under alkaline conditions, at above pH 8.5, since otherwise the carboxypeptidase Y exhibits greater peptidase activity than amidating activity and the yield of amidation product will be correspondingly small. The optimum pH for the reaction is in the range of 9.0 to 9.5.

The ammonia required for the amidating reaction is preferably provided in the form of a highly concentrated ammonia solution. Such a solution can be prepared, for example, by adding an alkali to an aqueous solution of an ammonium salt, thus raising the pH of the solution to within the range mentioned above. The ammonium salt used in this embodiment is preferably ammonium chloride, though other ammonium salts such as ammonium sulfate may also be used. For example, a 4.5 M ammonia solution can be obtained by adding 8.1 g of solid sodium hydroxide to 100 ml of 5 M aqueous ammonium chloride solution, thus adjusting its pH to 9.2. Similar results can be obtained by using another alkali, such as potassium hydroxide or lithium hydroxide, instead of the sodium hydroxide, for raising the pH of the ammonium salt solution. A 7.1 M ammonia solution can also be obtained, for example, by adding 27 ml of 25% aqueous ammonia to 100 ml of 5 M aqueous ammonium chloride solution, again raising the pH to 9.2.

In an alternative embodiment, the ammonia solution used for the amidation reaction can be obtained by lowering the pH of aqueous ammonia with an acid. For example, approximately 7 M ammonia solution can be obtained by adding hydrochloric acid to 25% aqueous ammonia solution, thus lowering the pH to 9.2.

In principle, the use of a very high ammonia concentration is desirable, in order to maximise the yield of amidation product. However, in practice the ammonia concentration is limited to a maximum of about 4.5 M in a system such as ammonium chloride/sodium hydroxide, because of the limited solubility of the ammonium salt. Although higher ammonia concentrations, of around 7 M, may be achieved by using the ammonia/hydrochloric acid system, nevertheless the yield of amidation product is considerably reduced by comparison with the other system, typically by around 30%, possibly due to a lower effective concentration of available ammonia in the reaction mixture.

The overall concentration of ammonia in the reaction mixture will be reduced if the ammonia solution is mixed with an aqueous solution of the peptide substrate and of the carboxypeptidase Y — for example, from an ammonia concentration of 4.5 M to 3.6 M. However, the substrate and the enzyme may themselves be dissolved in a 4.5 M ammonia solution, so as to maintain the ammonia concentration in the reaction mixture at 4.5M and thus maximise the yield of amidation product. Typically, the solution of substrate, enzyme and ammonia may be mixed in a ratio of about 1:1:8, and the concentrations of the substrate and enzyme in the reaction mixture may typically be about 1 mM and about 5 $\mu$m respectively.

The reaction time is not critical, but will normally be in the range of 3 to 5 hours. Conventional separation techniques, such as ion exchange column chromatography or high performance liquid chromatography, can be used to identify the amidation product in the reaction mixture, and to isolate and purify it at the end of the reaction period. An amino acid analyser can also be used to identify the presence of free amino acids formed during the reaction.

The invention will be further described by reference to the following Examples and Comparative Example. It is to be noted that the amidation reaction proceeds successfully with the peptide substrates of Examples 1 to 6, which all have a hydrophobic amino acid residue at the C-terminus. On the other hand, no amidation occurs with the substrate of the Comparative Example, having a hydrophilic C-terminal amino acid residue (i.e. glycine). This is in direct contrast to the results obtained by the prior art procedure of K. Breddam et al.

In the Examples and Comparative Example, the carboxypeptidase Y used was a product of the Peptide Institute, Inc., Osaka, Japan. In the peptide substrates, the abbreviation CBZ stands for the carbobenzoxy protecting group, and the abbreviations Ala, Leu, Ile, Val, Phe, Gly and Pro have the conventional meanings of alanine, leucine, isoleucine, valine, phenylalanine, glycine and proline, respectively.

EXAMPLE 1

A 7.1 mM solution of CBZ-Ala-Pro-Leu-OH was made up in 40% aqueous dioxane. Carboxypeptidase Y was dissolved in water to a concentration of 3.5 mg/ml (50 $\mu$M). A 4.5 M ammonia solution was prepared by adding solid sodium hydroxide to a 5 M aqueous solution of ammonium chloride until its pH was 9.5.

These three solutions, namely 200 $\mu$l of the peptide substrate solution, 200 $\mu$l of the carboxypeptidase Y solution and 1600 $\mu$l of the ammonia solution, were mixed together (the ammonia concentration in the mixture being 3.6 M) and incubated for 5 hours at 37° C.

After completion of the reaction, 300 $\mu$l of the reaction solution was extracted with 300 $\mu$l of ethyl acetate. The ethyl acetate layer was evaporated to dryness under reduced pressure, the residue was dissolved in 200 $\mu$l of 50% methanol/0.1% trifluoroacetic acid, and 100 $\mu$l of this solution was subjected to high performance liquid chromatography using a $\mu$Bondapak C18 column (0.39×30 cm). When eluted with 50% methanol/0.1% trifluoroacetic acid at a flow rate of 1 ml/minute, CBZ-Ala-Pro-NH$_2$ was detected after 4 minutes by monitoring UV absorption at 260 nm.

A further 300 $\mu$l of the reaction solution was acidified to pH2-3 with 60 $\mu$l of concentrated hydrochloric acid, and 180 $\mu$l of this solution was subjected directly to high performance liquid chromatography (without ethyl acetate extraction) using the same column as before. When eluted with 30% methanol/0.1% trifluoroacetic acid at a flow rate of 1 ml/minute, CBZ-Ala-Pro- $NH_2$, CBZ-Ala-Pro-OH and CBZ-Ala-Pro-Leu-OH were respectively detected after 7.9, 10 and 20.7 minutes by monitoring UV absorption at 260 nm.

The yield of each of these products was calculated from the ratio of the respective area under the trace on the high performance liquid chromatogram to the area produced by a standard sample on the same chromatogram. The yields relative to the amount of the initial substrate were calculated to be 35.1% for the amidation product, CBZ-Ala-Pro-$NH_2$, 19.5% for the side-product, CBZ-Ala-Pro-OH, and about 45% for the remaining unreacted substrate. As a cross-check, 10 μl of the reaction solution was directly subjected to amino acid analysis using a Hitachi Type 835 high speed amino acid analyzer, and its free leucine content was found to be about 55% relative to the amount of the initial substrate. This yield of leucine corresponds to the sum of the yields of the amidation product, CBZ-Ala-Pro-$NH_2$, and the side-product, CBZ-Ala-Pro-OH.

EXAMPLE 2

A 4.5 M ammonia solution was prepared by adding solid sodium hydroxide to a 5 M aqueous solution of ammonium chloride, until its pH was 9.2. A 7.1 mM solution of CBZ-Ala-Pro-Leu-OH was made up in 40% aqueous dioxane/ammonia solution. Carboxypeptidase Y was dissolved in ammonia solution to a concentration of 3.5 mg/ml (50 μM).

These three solutions, namely 200 μl of the peptide substrate solution, 200 μl of the carboxypeptidase Y solution and 1600 μl of the ammonia solution, were mixed together (the ammonia concentration in the mixture being 4.32 M) and incubated for 5 hours at 37° C.

After completion of the reaction, the reaction solution was extracted with an equal volume of ethyl acetate, and the ethyl acetate layer was evaporated to dryness. The residue was dissolved in 1 ml of 50% methanol/0.1% trifluoroacetic acid and subjected to high performance liquid chromatography using a μBondapak C18 column (0.36×30 cm). Elution with 50% methanol/0.1% trifluoroacetic acid at a flow rate of 1 ml/minute gave a purified amidation product, CBZ-Ala-Pro-$NH_2$, in 43% yield relative to the initial substrate.

EXAMPLE 3

A 7.1 mM solution of CBZ-Ala-Pro-Val-OH was made up in 40% aqueous dioxane. Carboxypeptidase Y was dissolved in water to a concentration of 3.5 mg/ml (50 μM). A 4.5 M ammonia solution was prepared by adding solid sodium hydroxide to a 5 M aqueous solution of ammonium chloride until its pH was 9.5.

These three solutions, namely 200 μl of the peptide substrate solution, 200 μl of the carboxypeptidase Y solution and 1600 μl of the ammonia solution, were mixed together (the ammonia concentration in the mixture being 3.6 M) and incubated for 5 hours at 37° C. After completion of the reaction, 300 μl of the reaction solution was extracted with 300 μl of ethyl acetate, and the ethyl acetate layer was evaporated to dryness under reduced pressure. The residue was dissolved in 200 μl of 50% methanol/0.1% trifluoroacetic acid, and 100 μl of this solution was subjected to high performance liquid chromatography using a μBondapak C18 column (0.39×30 cm). When eluted with 50% methanol/0.1% trifluoroacetic acid at a rate of 1 ml/minute, the amidation product, CBZ-Ala-Pro-$NH_2$, was detected after 4 minutes by monitoring UV absorption at 260 nm. The yield was 15.4%.

EXAMPLE 4

A 7.1 mM solution of CBZ-Ala-Pro-Phe-OH was made up in 40% aqueous dioxane. Carboxypeptidase Y was dissolved in water to a concentration of 3.5 mg/ml (50 μM). A 4.5 M ammonia solution was prepared by adding solid sodium hydroxide to a 5 M aqueous solution of ammonium chloride until the pH was 9.5.

These three solutions, namely 200 μl of the substrate solution, 200 μl of the carboxypeptidase Y solution and 1600 μl of the ammonia solution, were mixed together (the ammonia concentration in the mixture being 3.6 M) and incubated for 5 hours at 37° C.

After completion of the reaction, 300 μl of the reaction solution was extracted with 300 μl of ethyl acetate, and the ethyl acetate was evaporated to dryness under reduced pressure. The residue was dissolved in 200 μl of 50% methanol/0.1% trifluoroacetic acid, and 100 μl of this solution was subjected to high performance liquid chromatography using a μBondapak C18 column (0.39×30 cm). When eluted with 50% methanol/0.1% trifluoroacetic acid at a rate of 1 ml/minute, the amidation project, CBZ-Ala-Pro-$NH_2$, was detected after 4 minutes by monitoring UV absorption at 260 nm. The yield was 13.4%.

EXAMPLE 5

The amidation reaction of Example 1 was repeated, but using CBZ-Ala-Pro-Ile-OH as the peptide substrate. The amidation product, CBZ-Ala-Pro-$NH_2$, was obtained with a yield of 22.6%.

EXAMPLE 6

Human calcitonin-Leu peptide, produced by genetic engineering, was first subjected to reversible S-sulfonation by the method of R. David Cole (Methods in Enzymology, Vol. II, Ed. C.H.W. Hirs, pp 206 (1967), Academic Press, New York and London). This S-sulfonation of its disulfide linkage is aimed at preventing the sample from insolubilizing in the reaction solution.

A 4.5 M ammonia solution was prepared by adding solid sodium hydroxide to a 5 M aqueous solution of ammonium chloride until the pH was 9.5. A 1.7 mM solution of the S-sulfonated human calcitonin-Leu peptide was made up in 40% aqueous dimethylsulfoxide/ammonia solution. Carboxypeptidase Y was dissolved in the ammonia solution to a concentration of 3.5 mg/ml (50 μM).

These three solutions, namely 50 μl of the peptide substrate solution, 50 μl of the carboxypeptidase solution and 400 μl of the ammonia solution, were mixed together (the ammonia concentration in the mixture being 4.32 M) and incubated for 30 minutes at 37° C.

The reaction was then stopped by adding 100 μl of concentrated formic acid and 1500 μl of 8 M urea solution; and 210 μl of the resulting reaction solution was subjected to high performance liquid chromatography using a 4.6×250 mm column packed with TSK gel ODS-120T (Toyo Soda Ind.). The column was eluted with Solvent A, 10 mM ammonium bicarbonate solution, and Solvent B, acetonitrile, by the direct gradient method for Solvent B(0–10%, 0–4 minutes; 10–55%, 4–60 minutes), at a flow rate of 0.8 ml/minute. The amidation product, the unreacted substrate and non-amidated side-product were detected after 37.15 minutes, 36.16 minutes and 35.17 minutes, respectively, by monitoring UV absorption at 225 nm.

The yield of each of these products was calculated from the ratio of the respective area under the trace on the high performance liquid chromatogram to the area produced by a standard sample on the same chromatogram. The yields relative to the initial substrate were calculated to be 24.7% for the amidation product, S-sulfonated human calcitonin, 57% for unreacted substrate, and 17.2% for the side-product.

S-sulfonated human calcitonin, the amidation product, was alllowed to react in 10 mM ammonium bicarbonate solution (pH 7.9) at room temperature for 7 hours in the presence of 2 mM glutathione (reduced type) and 1 mM ethylenediaminetetraacetic acid disodium salt to give a mature human calcitonin.

COMPARATIVE EXAMPLE

CBZ-Ala-Pro-Gly-OH was used as the peptide substrate in the procedure of Example 1. No amidation reaction occurred and the unreacted substrate was recovered at the end of the procedure.

I claim:

1. A process for the preparation of a peptide having C-terminal proline amide, which comprises reacting in aqueous solution a peptide substrate having a C-terminus selected from the group consisting of prolyl-leucine, prolyl-isoleucine, prolyl-valine, and prolyl-phenylalanine with carboxypeptidase Y in the presence of ammonia.

2. A process as claimed in Claim 1, in which the ammonia is generated by reaction of an ammonium salt with an alkali.

3. A process as claimed in Claim 2, in which said alkali is selected from the group consisting of sodium hydroxide, potassium hydroxide and lithium hydroxide.

4. A process as claimed in Claim 2, in which the ammonia concentration in the reaction mixture is in the range of from about 3.6 M to about 4.5 M.

5. A process as claimed in Claim 1, in which the molar ratio of carboxypeptidase Y to peptide substrate in the reaction mixture is in the range of from about 5:1000 to about 50:1000.

6. A process as claimed in Claim 1, in which the peptide produced is human calcitonin.

* * * * *